United States Patent
Julius

[11] Patent Number: 5,861,513
[45] Date of Patent: Jan. 19, 1999

[54] PREPARATION OF 1-ACETYL-4-PIPERIDONES

[75] Inventor: Manfred Julius, Limburgerhof, Germany

[73] Assignee: BASF Aktiengesellschaft, Ludwigshafen, Germany

[21] Appl. No.: 911,173

[22] Filed: Aug. 14, 1997

[30] Foreign Application Priority Data

Aug. 23, 1996 [DE] Germany ......................... 196 34 147.7

[51] Int. Cl.$^6$ ................................................ C07D 211/44
[52] U.S. Cl. ............................................ 546/242; 546/16
[58] Field of Search ....................... 546/242, 16

[56] References Cited

U.S. PATENT DOCUMENTS

| | | | |
|---|---|---|---|
| 3,043,862 | 7/1962 | Altenschoepfer | 260/488 |
| 3,860,628 | 1/1975 | Shuman | 260/465 D |
| 3,886,117 | 5/1975 | Havinga | 260/45.85 N |
| 3,886,212 | 5/1975 | Kunstle | 260/561 R |
| 4,562,152 | 12/1985 | Kleemann | 435/116 |
| 5,344,979 | 9/1994 | Zey | 564/216 |

FOREIGN PATENT DOCUMENTS

| | | |
|---|---|---|
| 1121605 | 6/1959 | Germany . |
| 3800987 | 3/1996 | Germany . |

*Primary Examiner*—Evelyn Huang
*Attorney, Agent, or Firm*—Keil & Weinkauf

[57] ABSTRACT

A process for preparing 1-acetyl-4-piperidones of the formula I

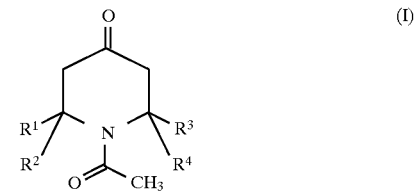

where $R^1$, $R^2$, $R^3$ and/or $R^4$ are each a $C_1$- to $C_6$-alkyl group or $R^1$ and $R^2$ together or/and $R^3$ and $R^4$ together are an alicyclic hydrocarbon chain having from 2 to 5 carbons, comprises reacting a component comprising the corresponding nonacetylated 4-piperidone with ketene in the presence of a component comprising an acid catalyst at from 20° C. to 120° C.

8 Claims, No Drawings

PREPARATION OF 1-ACETYL-4-PIPERIDONES

The present invention relates to a process for preparing 1-acetyl4-piperidones of the formula I

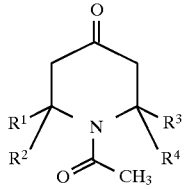

where $R^1$, $R^2$, $R^3$ and/or $R^4$ are each a $C_1$- to $C_6$-alkyl group or $R^1$ and $R^2$ together or/and $R^3$ and $R^4$ together are an alicyclic hydrocarbon chain having from 2 to 5 carbons; more particularly to a process for preparing 1-acetyl-2,2,6,6-tetramethyl-4-piperidone (N-acetyltriacetoneamine; abbreviated N-acetyl-TAA).

N-Acetyl-TAA is known as an intermediate for the synthesis of hindered amine heat and light stabilizers, which play an important role as additives for stabilizing plastics such as polyolefins.

N-Acetyl-TAA can be prepared by acetylating triacetoneamine with acetyl chloride or with acetic anhydride. However, acetylating triacetoneamine in this way is difficult and tends to lead to resinification.

To solve this problem, DE-C 38 00 987 discloses a process for preparing N-acetyltriacetoneamine by reacting triacetoneamine with acetic anhydride in a molar ratio of from 1:2.5 to 1:10 at temperatures of from 80 to 140° C. and continuously distilling off the resulting acetic acid with or without the solvent.

The excess of acetic anhydride required, however, is a disadvantage of this known process in that acetic anhydride has to be recovered from each batch. A further disadvantage is the high reaction temperature of generally 110° C.

In addition to these known acetylating agents, ketene can be used for acetylation. When reacting ketene as acetylating agent with carbonyl compounds, beta-lactones or enol acetates are formed. DE-B 1 121 605 discloses that, in the reaction of carbonyl compounds with ketene, the formation of enol acetates can be promoted by allowing the enolizable carbonyl compound, for example acetone, to react at from 20° to 110° C. in the presence of a catalyst comprising difluorophosphoric acid or a mixture of equimolar amounts of difluorophosphoric acid and monofluorophosphoric acid or the reaction product of phosphorus pentoxide with hydrogen fluoride. Under these reaction conditions, more than 80% of the carbonyl compound is converted into the corresponding O-acetylated enols.

It is an object of the present invention to provide a simple and economical process for preparing 1-acetyl4-piperidones of the aforementioned formula I by acetylating the 4-piperidone at the nitrogen and at the same time avoiding the formation of O-acetylated enols.

We have found that this object is achieved by a process for preparing 1-acetyl-4-piperidones of the formula I

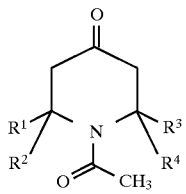

where $R^1$, $R^2$, $R^3$ and/or $R^4$ are each a $C_1$- to $C_6$-alkyl group or p1 $R^1$ and $R^2$ together or/and $R^3$ and $R^4$ together are an alicyclic hydrocarbon chain having from 2 to 5 carbons, which comprises reacting a component comprising the corresponding nonacetylated 4-piperidone with ketene in the presence of a component comprising an acid catalyst at from 20° C. to 120° C.

The essence of the process according to the invention is that the formation of O-acetylated enols described in the literature in a general way for carbonyl compounds does not occur in the reaction of ketene with nonacetylated 4-piperidones, in particular with triacetoneamine, in the presence of an acid catalyst. On the contrary, under these specific reaction conditions, acetylation of triacetoneamine at the nitrogen takes place preferentially. A further advantage of the process according to the invention is its excellent selectivity, which is more than 90%.

In the process according to the invention, preference is given to using an acid catalyst having a $pK_a$ of less than 4.7, in particular difluorophosphoric acid. The proportion of this catalyst, based on the starting material, is preferably from 0.1 to 10 mol %, particularly preferably from 1 to 5 mol %. When difluorophosphoric acid is used, a proportion of from 1 to 3 mol % is very particularly preferred. Suitable solvents for the reaction are polar or apolar, inert, aprotic organic solvents, for example hydrocarbons or ethers. Preference is given to using ethers, in particular tetrahyrofuran. However, if necessary, the reaction can also be carried out without solvent.

As already mentioned, the reaction is very selective, in particular when the strong acid difluorophosphoric acid is employed. However, other strong acids, such as hexafluorophosphoric acid, sulfuric acid, phosphoric acid, chlorosulfonic acid, p-toluenesulfonic acid and boron trifluoride containing traces of water, i.e. hydrofluoric acid, can also be used. This is particularly surprising since carbonyl compounds, under comparable reaction conditions, react with ketene in the presence of such a catalyst to afford the corresponding O-acetylated enols ("enol acetates").

Conventional catalysts, for example known amines such as 1,8-diazabicyclo[5.4.0]undec-7-ene (DBU) and 4-dimethylaminopyridine (DMAP) or even acetic acid ($pK_a$=4.75), are unsuitable for this purpose.

The Example which follows illustrates the invention:

EXAMPLE 1

Synthesis of 1-acetyl-2,2,6,6-tetramethyl-4-piperidone (N-acetyltriacetoneamine, N-acetyl-TAA)

In a 0.5 l four-neck flask, a solution of 31.0 g (0.20 mol) of TAA [purity by GC: 99.6 area %] in 250 ml of dry tetrahydrofuran was admixed with 0.44 g (0.28 ml; 4 mmol) of difluorophosphoric acid hydrate ($HF_2PO_2 \times 0.5\ H_2O$). A stream of ketene gas of about 0.5 mol/h was passed into this solution, and within 1 h the reaction solution was heated with stirring to 46°–48° C. (bath temperature: 55° C.) when a slow ketene breakthrough was observed. After the introduction of ketene had ended, the solution was cooled to room temperature and admixed with 1.0 g of sodium acetate by stirring. The solution was decanted from any undissolved salt and concentrated at 100-20 mbar and 50° C. The crude product (a light-brown solid) had the following composition by GC (area %): 94.3% of N-acetyl-TAA, 2.6% of TAA, 3.1% remainder. This corresponds to a TAA conversion of 97.4% with a selectivity of 96.8% based on TAA. Distillation at 0.4 mbar afforded an N-acetyl-TAA main fraction of a purity of 95.3% (29.1 g) and a further fraction of a purity of 80.4% (2.7 g). This corresponds to a yield of 76%. Recrystallization of the main fraction from 60 ml of n-hexane gave 25.9 g of yellowish N-acetyl-TAA of a purity of 99.6%.

m.p.: 56°–61° C.

Examination by $^{13}$C-NMR (100 Mhz, $CDCl_3$) gave the following results:

δ = 28.41 (q, CO<u>C</u>H₃), 30.36 (q, C(<u>C</u>H₃)₂), 54.07 (t, CH₂), 56.80 (s, <u>C</u>(CH₃)₂), 173.75 (s, N<u>C</u>OCH₃), 207.78 (s, C = 0)

We claim:
1. A process for preparing 1-acetyl-4-piperidones of the formula I

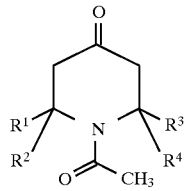

where $R^1$, $R^2$, $R^3$ and/or $R^4$ are each a $C_1$- to $C_6$-alkyl group or $R^1$ and $R^2$ together or/and $R^3$ and $R^4$ together are an alicyclic hydrocarbon chain having from 2 to 5 carbons, which comprises reacting the corresponding nonacetylated 4-piperidone with ketene in the presence of a strong acid catalyst at from 20° C. to 120° C. wherein the selectivity for the compound of Formula I is greater than 90%.

2. The process as claimed in claim 1, wherein $R^1$, $R^2$, $R^3$ and $R^4$ are each $C_1$- to $C_3$-alkyl.

3. The process as claimed in claim 1, wherein the acid catalyst used is an acid having a $pK_a > 4.7$ in an amount of from 0.1 to 10 mol %.

4. The process as claimed in claim 1, wherein the reaction is carried out at from 30° to 50° as solvent.

5. The process as claimed in claim 1, wherein the catalyst used is difluorophosphoric acid.

6. The process of claim 2, wherein $R^1$, $R^2$, $R^3$ an $R^4$ are each methyl.

7. The process of claim 4, wherein the reaction is carried out in tetrahydrofuran as a solvent.

8. The process of claim 1 wherein the strong acid catalyst is difluorophosphonic acid, hexafluorophosphoric acid, sulfuric acid, phosphoric acid, chlorosulfonic acid, p-toluenesulfonic acid or boron trifluoride containing traces of water, i.e. hydrofluoric acid.

* * * * *

UNITED STATES PATENT AND TRADEMARK OFFICE
CERTIFICATE OF CORRECTION

PATENT NO.: 5,861,513

DATED: January 19, 1999

INVENTOR(S): Manfred JULIUS

It is certified that error appears in the above-identified patent and that said Letters Patent is hereby corrected as shown below:

Col. 4, claim 3, line 9, "$pK_a > 4.7$" should be --$pK_a < 4.7$--.

Signed and Sealed this

Twenty-fifth Day of May, 1999

Attest:

Q. TODD DICKINSON

*Attesting Officer*   *Acting Commissioner of Patents and Trademarks*